United States Patent [19]

Haas et al.

[11] 4,278,803
[45] Jul. 14, 1981

[54] PREPARATION OF 2-METHYLENE-1,3-PROPANEDIAMIDE

[75] Inventors: Howard C. Haas, Arlington; Stanley J. Jasne, Andover, both of Mass.; Robert D. Moreau, Nashua, N.H.

[73] Assignee: Polaroid Corporation, Cambridge, Mass.

[21] Appl. No.: 109,811

[22] Filed: Jan. 7, 1980

[51] Int. Cl.³ .................. C07F 7/08; C07C 102/00
[52] U.S. Cl. .............................. 556/419; 564/160
[58] Field of Search .......... 260/561 A, 561 K, 561 N; 556/419; 564/160

[56] References Cited

U.S. PATENT DOCUMENTS

| | | | |
|---|---|---|---|
| 2,466,395 | 4/1949 | Dickey | 260/78.5 |
| 2,741,631 | 4/1956 | Saver | 260/561 N |
| 2,774,778 | 12/1956 | Sommer | 556/419 |
| 3,247,280 | 4/1966 | Kanner | 260/561 A |
| 3,546,270 | 12/1970 | Kirchmayr et al. | 260/561 N |

FOREIGN PATENT DOCUMENTS 679812  2/1964  Canada ................................. 556/419

OTHER PUBLICATIONS

Eberson, Acta Chem. Scand. 10(1956), pp. 633–637.
Jarvie, Organochem. Rev. (A) 6 (1970), pp. 153–207.
Cunico, J. Am. Chem. Soc. 94(1972), p. 2868.
Chan et al., Tet. Let. 1974#2, p. 171.
Chan et al., Tet. Let. 1974#39, p. 3511.

*Primary Examiner*—Arthur P. Demers
*Attorney, Agent, or Firm*—John J. Wasatonic

[57] ABSTRACT

A process for preparing 2-methylene-1,3-propanediamide is disclosed which comprises providing a solution of a novel compound of the formula

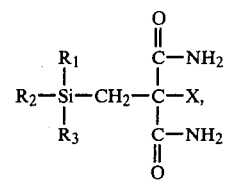

wherein $R_1$, $R_2$, and $R_3$ can each independently be lower alkyl of from 1 to 10 carbon atoms, aryl, alkaryl, aralkyl, or halogen and X is an electron-accepting leaving group, in an inert, aprotic organic solvent, and subjecting the compound in solution to β-elimination reaction conditions effective to eliminate the silyl group

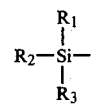

and the electron-accepting leaving group

—X from the compound to form a double bond between those carbon atoms to which the silyl group and the electron-accepting leaving group were bonded, thereby forming 2-methylene-1,3-propanediamide. 2-Methylene-1,3-propanediamide is useful in preparing polymers which can be used in preparing coating compositions, films, and filaments.

16 Claims, No Drawings

PREPARATION OF 2-METHYLENE-1,3-PROPANEDIAMIDE

BACKGROUND OF THE INVENTION

This invention relates to the preparation of 2-methylene-1,3-propanediamide. More particularly, it relates to a process for preparing this monomer by a β-elimination reaction conducted in the presence of an inert, aprotic organic solvent.

U.S. Pat. No. 2,466,395, issued to J. B. Dickey, discloses the use of 2-methylene-1,3-propanediamide or, more commonly, methylene malonamide, as a comonomer for preparing copolymers useful in preparing films and filaments. The process for preparing this monomer, disclosed therein, is said to comprise a sulfuric acid or hydrogen peroxide hydrolysis of 2-methylenepropanedinitrile, i.e.,

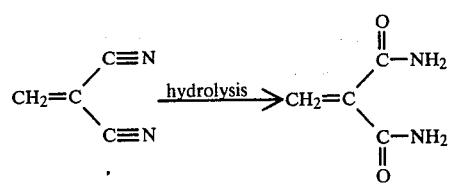

This preparative method has certain inherent disadvantages. One disadvantage is that 2-methylene-1,3-propanediamide tends to be unstable in the presence of such reagents as sulfuric acid and hydrogen peroxide, the monomer tending to undergo polymerization or other degradative reactions in the presence of such reagents. Thus, the reaction conditions suggested by U.S. Pat. No. 2,466,395 for preparing this monomer are generally unfavorable in terms of obtaining the desired product and especially in terms of obtaining a high yield of the desired product.

Another disadvantage of the process disclosed in U.S. Pat. No. 2,466,395 is that 2-methylenepropanedinitrile is highly toxic and, as such, is an undesirable intermediate.

The present invention avoids the aforementioned problems and disadvantages by providing a novel process for preparing 2-methylene-1,3-propanediamide which avoids the use of 2-methylenepropanedinitrile and the use of reagents which tend to degrade the product monomer and which is capable of providing the desired product in repeatedly good yield and purity.

It is thus an object of the present invention to provide a process for preparing 2-methylene-1,3-propanediamide.

It is another object of the present invention to provide a process for preparing 2-methylene-1,3-propanediamide with minimal concurrent derivatization or polymerization of the product monomer.

Other objects of this invention will in part be obvious and will in part appear hereinafter.

'SUMMARY OF THE INVENTION

The present invention provides a novel process for preparing the monomer 2-methylene-1,3-propanediamide which comprises providing a solution of a compound of the formula

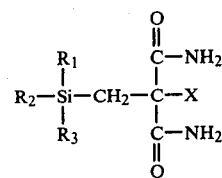

where $R_1$, $R_2$, and $R_3$ each can independently be lower alkyl of from 1 to 10 carbon atoms, aryl, alkaryl, aralkyl, or halogen, and X is an electron-accepting leaving group, in an inert, aprotic organic solvent, and subjecting the compound in solution to β-elimination reaction conditions effective to eliminate the silyl group $$R_2-\underset{\underset{R_3}{|}}{\overset{\overset{R_1}{|}}{Si}}-$$

and the electron-accepting leaving group

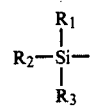

from the compound to form a double bond between those carbon atoms to which the silyl and the electron-accepting leaving groups were bonded, thereby forming 2-methylene-1,3-propanediamide. It has been found that the conduct of the aforesaid β-elimination process permits the production of 2-methylene-1,3-propanediamide in high yield and with minimized polymerization and derivatization thereof.

For a fuller understanding of the nature and objects of this invention, reference should be had to the following detailed description.

DETAILED DESCRIPTION OF THE INVENTION

Preparation of 2-methylene-1,3-propanediamide tends to be difficult because of the high reactivity of this monomer. For example, it has been found to be sensitive to protic materials whereby the monomer is derivatized by addition of the protic material across the double bond, e.g.,

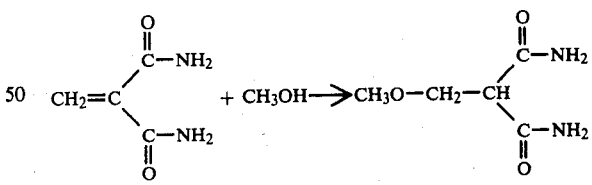

Such derivatization reactions are generally also accompanied by some degree of polymerization of the monomer. In addition, the monomer has been found to readily undergo anionic and free radical polymerization reactions such that preparation and isolation of the monomer without a substantial degree of concurrent polymerization tends to be difficult.

The present invention provides a novel process for preparing 2-methylene-1,3-propanediamide which is capable of providing the desired monomer in high yield with minimal derivatization or polymerization. This process has proven to be a particularly advantageous method of preparing this monomer since the high reactivity of the monomer tends to render other potential methods of preparation either impractical or inoperative.

The process of the present invention comprises providing a solution of a compound of the formula

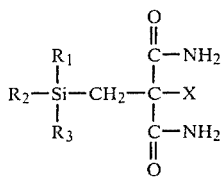

where $R_1$, $R_2$ and $R_3$ each can independently be lower alkyl of from 1 to 10 carbon atoms, aryl, alkaryl, aralkyl, or halogen, and X is an electron-accepting leaving group, in an inert, aprotic organic solvent, and subjecting the compound in solution to $\beta$-elimination reaction conditions effective to eliminate the silyl group

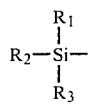

and the electron-accepting leaving group

—X from the compound to form a double bond between those carbon atoms to which the silyl group and the electron-accepting leaving group were bonded, thereby forming 2-methylene-1,3-propanediamide.

The removal of the silyl group and the electron-accepting leaving group situated $\beta$ thereto from the starting material to form the desired carbon-carbon double bond constitutes a $\beta$-elimination reaction. Thus, by the term "$\beta$-elimination reaction" is meant a reaction involving the elimination or removal of two groups from a parent molecule, said groups being substituted on the parent molecule on adjacent carbon atoms, i.e., $\beta$ to each other, with the elimination or removal resulting in the formation of a double bond between the adjacent carbon atoms.

As used herein, the term "$\beta$-elimination reaction conditions" denotes those conditions to which the starting material, dissolved in an inert, aprotic organic solvent, is subjected in order to effect elimination of the silyl group and the electron-accepting leaving group X from the molecule. Suitable $\beta$-elimination reaction conditions include, for example, subjecting the starting material to various conditions of time and temperature, or subjecting the starting material to an initiating agent capable of promoting the desired reaction. Thus, for example, the $\beta$-elimination reaction can be thermally initiated by heating the reaction solution to a temperature sufficient to induce the elimination of the silyl group and the electron-accepting leaving group from the starting material to form the desired monomer. Alternatively, various initiating agents can be used to promote the reaction by causing or aiding in the elimination of the silyl group or the electron-accepting leaving group from the starting material.

In view of the high reactivity of the product monomer, and for purposes of maximizing the yield of the $\beta$-elimination reaction, it is preferred that the $\beta$-elimination reaction conditions be such that concurrent derivatization and polymerization of the product monomer is minimized. Thus, in a thermally initiated $\beta$-elimination reaction the temperature should be sufficient to induce the elimination of the desired groups from the starting material but preferably insufficient to also cause a substantial amount of derivatization or polymerization of the product monomer. Similarly, it is preferred that any initiating agent utilized to promote the reaction be otherwise substantially inert and incapable of substantially derivatizing or inducing the polymerization of the monomer.

With respect to the preferred utilization of reaction conditions which minimize the polymerization and derivatization of the monomer, the use of the novel silyl derivatized starting material

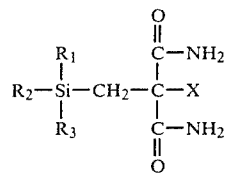

hereinafter referred to as the starting material, has been discovered to be particularly advantageous inasmuch as abstraction or elimination of the silyl group

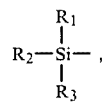

as a necessary mechanistic step in the formation of the desired double bond, can be accomplished under relatively mild reaction conditions in the presence of an inert, aprotic organic solvent and in the absence of materials reactive with the unsaturated monomer. It is believed that the low electronegativity of silicon versus carbon promotes removal of the silyl group and cleavage of the carbon-silicon bond by allowing facile transfer of electrons to the more electronegative carbon atom. This facile C—Si bond cleavage thus allows the use of the preferred reaction conditions of the present process. Further, the cleavage of the C—Si bond is believed to in turn facilitate the C—X bond cleavage by providing electrons for transfer to the electron-accepting leaving group X.

The substituents on the silicon atom, $R_1$, $R_2$ and $R_3$ can each independently be lower alkyl of from 1 to 10 carbon atoms (e.g., methyl, ethyl, propyl, isopropyl); aryl (e.g., phenyl, naphthyl); alkaryl (e.g., tolyl); aralkyl (e.g. benzyl); or halogen (e.g., chloro, bromo, iodo). In a preferred embodiment of the present invention, each of $R_1$, $R_2$, and $R_3$ is lower alkyl of from 1 to 10 carbon atoms. Most preferably, each of $R_1$, $R_2$, and $R_3$ is methyl. It will be appreciated that methyl groups provide minimal steric interference about the silicon atom as compared to that provided by more bulky substituents. Such steric interference may have an affect on the rate of reaction in those cases where the reaction involves an interaction between the silicon atom and an initiating agent such as, for example, a nucleophile.

The leaving group X can be any group capable of accepting electrons from the starting material such that cleavage of the C—X bond occurs to effect removal or elimination of X from the starting material. Suitable electron-accepting leaving groups include chloride, bromide, and iodide; hydroxy; alkoxy; thiol; thioethers;

sulfonyl, in particular, p-toluenesulfonyl; quaternary nitrogen groups; phosphonium groups; and

wherein R can be alkyl or aryl. The particular leaving group used is not critical provided that it is capable of departing from the starting material with the bonding electron pair. A study of electron-accepting leaving groups is provided by C. J. M. Stirling, Acc. Chem. Res., 12, 198 (1979).

A preferred electron-accepting leaving group from a preparative standpoint is chloride. It has been discovered that chloride is readily eliminated from the starting material in thermally induced β-elimination reactions and in β-elimination reactions induced by initiating agents, as detailed in the examples contained hereinafter.

The process of the present invention is conducted in the presence of an inert, aprotic organic solvent. Such a solvent system is necessary due to the aforementioned tendency of the product 2-methylene-1,3-propanediamide to add protic solvents and reagents across the double bond and/or to undergo polymerization in the presence of such solvents and reagents. It may also be noted that the use of an inert aprotic solvent system is necessary inasmuch as attempts to effect the reaction of the present process by heating the starting material in the absence of a solvent, i.e., thermally "cracking" a melt of the starting material, were unsuccessful.

As used herein, the term "inert solvent" refers to any solvent which does not react chemically with any of the reactants or products of the reaction and which also is incapable of inducing or promoting polymerization of the monomer. For example, it has been discovered that the monomer can undergo some degree of polymerization in the presence of basic solvents. Accordingly, solvents useful in the present invention are preferably neutral or slightly acidic or at least are of a basicity insufficient to induce or promote polymerization of 2-methylene-1,3-propanediamide under the β-elimination reaction conditions being utilized. Similarly, such solvents should be substantially free of any impurities which may induce or promote polymerization of the monomer. For example, water is a protic material which can induce polymerization as well as add across the double bond. Thus, in general, the solvents employed herein should be substantially anhydrous. It may be noted, however, that in some cases a minimal amount of water may be tolerated or even beneficial, particularly when the presence of such a minimal amount of water may aid in or promote the solubilization of an initiating agent in the aprotic solvent.

As used herein, the term "aprotic solvent" refers to any solvent which is substantially incapable of acting as a proton donor or as an acid. Thus, these solvents will generally be incapable of reacting with 2-methylene-1,3-propanediamide or inducing polymerizaton thereof. Preferred aprotic solvents are those possessing a relatively high dielectric constant. Since the β-elimination reaction is generally believed to involve some degree of charge formation within the starting material, i.e., a partial positive charge formation on the silicon atom and a partial negative charge formation on the leaving group X, the reaction can be expected to proceed more readily in solvents which are able to promote and accommodate such charge formation. Aprotic solvents possessing a high dielectric constant will, of course, more readily accommodate such charge formation than will lower dielectric constant solvents and, thus, are preferred for use in the present invention. In general, the preferred aprotic solvents are those with a dielectric constant at room temperature of at least 15. Such preferred aprotic solvents include, for example, nitrated solvents such as nitromethane, nitroethane, and nitrobenzene; nitriles such as acetonitrile, propionitrile, and benzonitrile; ketones such as acetone and methylethylketone; amides such as formamide, N,N-dimethylformamide, N,N-dimethylacetamide and 1-methyl-2-pyrrolidinone; dimethylsulfoxide; and hexamethylphosphoramide. Dielectric constants of various aprotic solvents can be had by reference to Riddick and Bunger, *Techniques of Chemistry*, Vol. II, Organic Solvents, 3d. ed., John Wiley and Sons, Inc., 1970.

According to the present invention, a variety of β-elimination reaction conditions can be utilized to effect the elimination of the desired groups from the starting material. For example, the reaction solution can be heated to a temperature sufficient to cause the elimination of the silyl group and the electron-accepting leaving group to form the desired double bond. A suitable operating range of temperatures is about 50° C. to about 150° C. and is preferably about 80° C. to about 110° C. It has been found that the reaction can be conducted satisfactorily, for example, in refluxing nitromethane (b.p.=101° C.) as detailed in Example 2 hereinafter.

Suitable β-elimination reaction conditions herein also include subjecting the starting material in solution to initiating agents which promote the reaction by causing or aiding in the elimination of the silyl group or the electron-accepting leaving group from the starting material. It will be appreciated that the cleavage of the C—Si bond will promote C—X bond cleavage by providing electrons for transfer to X and that C—X bond cleavage will provide a positive charge on the starting material which promotes C—Si bond cleavage. Thus, any particular initiating agent effectively promotes elinination of both groups.

Materials known to promote β-elimination reactions which can be used in the present invention include Grignard reagents such as methylmagnesium bromide, and Lewis acids such as boron trifluoride, aluminum trichloride, and silver cation. Nucleophilic initiating agents may also be utilized in the present invention. It is preferred that the basicity or nucleophilicity of these initiating agents be insufficient to effect substantial polymerization or derivatization of the product monomer. The commonly assigned copending U.S. patent application of Sachdev, Ser. No. 109,812, filed Jan. 7, 1980, discloses fluoride anion as a particularly useful initiating agent for the production of 2-methylene-1,3-propanediamide.

Though it is not essential, it is preferred to conduct the β-elimination reaction under an inert atmosphere, such as nitrogen, to further ensure optimum yields. In addition, the introduction of a continuous stream of an inert gas may aid the reaction by removing the relatively low boiling silyl derivatives, formed as a result of the elimination of the silyl group from the starting material, from the reaction solution.

Subsequent to formation, the monomer may, if desired, be separated from the reaction mixture in any convenient manner as, for example, by precipitation followed by filtration, leaving the reaction by-products in the filtrate. Further purification may be achieved by trituration or recrystallization of the monomer as described in the examples given herein.

The starting materials used in the present invention are novel compounds and may be prepared, for example, by abstraction of the proton substituted at the 2-position of a 2-(trisubstituted silyl)methyldiamide and substitution therefore of the desired leaving group. Thus, sulfuryl chloride may be used to prepare a useful starting material wherein X is chloride:

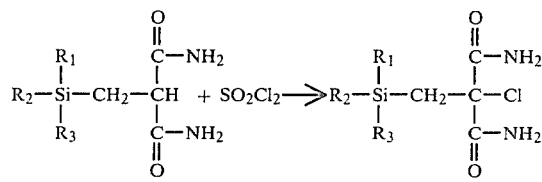

Similar proton abstraction and leaving group substitution may be achieved with other reactive species to produce novel materials having different leaving groups X. For example, bromination with molecular bromine or N-bromosuccinimide may be used to prepare a material wherein X is bromide. Reaction with lead tetraacetate or p-toluenesulfonyl chloride may be used to produce starting materials wherein X is, respectively, acetate or p-toluenesulfonyl.

The 2-(trisubstituted silyl)methyl-1,3,propanediamide shown in the above sulfuryl chloride reaction can be prepared, for example, by reaction of the corresponding diester of a 2-(trisubstituted silyl)methylpropanedioic acid with ammonia in methanol which contains a catalytic amount of sodium methoxide. The diester of a 2-(trisubstituted silyl)methylpropanedioic acid in turn can be prepared by reaction of the diester of propanedioic acid with an appropriate halomethylsilane in the presence of a base which is incapable of hydrolyzing the ester function. Thus, the following sequence of reactions can be used:

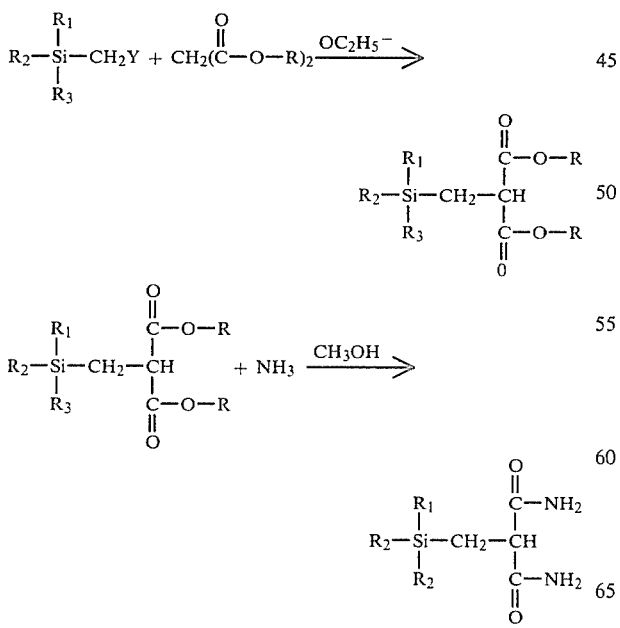

wherein Y is a halogen.

The following examples are given to further illustrate the present invention and are not intended to limit the scope thereof.

EXAMPLE 1

Preparation of 2-chloro-2-(trimethylsilyl)methyl-1,3-propanediamide 47 grams of 2-(trimethylsilyl)methyl-1,3-propane diamide were placed into a 3-necked, 3-liter flask fitted with a mechanical stirrer, dropping funnel, condenser, and drying tube filled with a dessicant. One liter of dry toluene was added and the reaction mixture allowed to stir at room temperature for one hour. One equilvalent (20 ml.) of freshly distilled sulfuryl chloride was dissolved in one liter of toluene and this solution added dropwise to the above reaction mixture.

After the addition was completed, the reaction mixture was stirred at room temperature for about 18 hours. The reaction mixture was then suction filtered and the recovered solid washed with 100 ml. of cold toluene. The solid was then air dried.

The solid was recrystallized from about 250 ml. of tetrahydrofuran. Precipitation was aided by the slow addition of about 25 ml. of petroleum ether. The recrystallized product was suction filtered, washed with cold petroleum ether and air dried to give 41.7 grams of white solid melting at 128° C.

Elemental analysis calculated for $C_7H_{15}ClN_2O_2Si$: C, 37.75; H, 6.8; Cl, 16.05; N, 12.39. Found: C, 38.06; H, 7.2; Cl, 15.91; N, 12.58.

EXAMPLE 2

Preparation of 2-methylene-1,3-propanediamide 1.95 grams of 2-chloro-2-(trimethylsilyl)methyl-1,3-propanediamide were added to 90 ml. of freshly distilled nitromethane and placed in a 250 ml., 3-necked flask fitted with gas inlet and outlet, magnetic stirrer, and reflux condenser. Nitrogen gas was bubbled into the solution for about 15 minutes at room temperature. Then, under continued nitrogen flow, the solution was heated at reflux for 2 hours. After cooling to room temperature the solution was filtered and precipitated into 450 ml. of toluene. The resulting solid was filtered and air dried giving 440 mg. of the desired monomer.

The solid filtered from the reaction solution was washed with 90 ml. of acetone which was concentrated to give an additional 40 mg. of monomer.

The above monomer samples were recrystallized from ethyl acetate-petroleum ether giving material melting at 149-151° C.

Elemental analysis calculated for $C_4H_6N_2O_2$: C, 42.10; H, 5.30; N, 24.55. Found: C, 42.13; H, 5.40; N, 24.30.

EXAMPLE 3

Preparation of 2-methylene-1,3-propanediamide

This example is reproduced from the above referenced copending U.S. patent application of Sachdev et al., Ser. No. 109,812:

44 Grams of 2-chloro-2-(trimethylsilyl)methyl-1,3-propanediamide were added to 3 liters of acetonitrile and stirred for one hour. Undissolved solids were removed by filtration. The solution was then placed in a 5-liter flask fitted with a drying tube filled with calcium chloride. 1.3 equivalents (24.4 grams) of potassium fluoride dihydrate and about 0.3 grams of dicyclohexyl-18- crown-6 were added and the reaction mixture stirred at a temperature of about 25° C. until nuclear magnetic resonance analysis indicated the absence of starting material.

The mixture was filtered and the solid obtained was washed with 1.5 liters of acetonitrile to remove monomer from the solid paste. The combined acetonitrile solutions were dried over magnesium sulfate and evaporated under vacuum at room temperature to give a white solid. This solid was triturated with methylene chloride until remaining traces of starting material were removed. The solid product was then dissolved in 2.5 liters of acetone, undissolved materials were filtered, and the acetone solution was concentrated under vacuum to give 16 grams of solid product. This product was recrystallized from a mixture of 1800 ml. of ethylacetate and 600 ml. of petroleum ether to give 12.7 grams of product melting at 149°–151° C.

2-Methylene-1,3-propanediamide is useful in preparing polymers which can be used in preparing coating compositions, films, and filaments.

What is claimed is:

1. A process for preparing 2-methylene-1,3-propanediamide, which comprises:

providing a solution of a compound of the formula

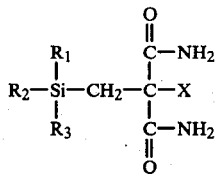

wherein $R_1$, $R_2$, and $R_3$ can each independently be lower alkyl of from 1 to 10 carbon atoms, aryl, alkaryl, aralkyl, or halogen, and X is an electron-accepting leaving group, in an inert, aprotic organic solvent;

subjecting said compound in said solution to β-elimination reaction conditions effective to eliminate the silyl group

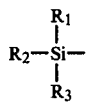

and the electron-accepting leaving group

—X from said compound to form a double bond between those carbon atoms to which the silyl group and the electron-accepting leaving group were bonded, thereby forming 2-methylene-1,3-propanediamide.

2. A process of claim 1 wherein each of $R_1$, $R_2$, and $R_3$ is lower alkyl of from 1 to 10 carbon atoms.

3. A process of claim 2 wherein each of $R_1$, $R_2$, and $R_3$ is methyl.

4. A process of claim 1 wherein X is chloride.

5. A process of claim 1 wherein the dielectric constant at room temperature of said inert, aprotic organic solvent is at least 15.

6. A process of claim 1 wherein said β-elimination reaction conditions comprise heating said solution.

7. A process of claim 6 wherein said solution is heated to between 50° C. and 150° C.

8. A process of claim 7 wherein said solution is heated to between 80° C. and 110° C.

9. A process of claim 8 wherein the dielectric constant at room temperature of said inert, aprotic organic solvent is at least 15.

10. A process of claim 9 wherein said inert, aprotic organic solvent is nitromethane.

11. A process of claim 1 wherein said β-elimination reaction conditions comprise subjecting said compound in said solution to an initiating agent capable of promoting said elimination of said silyl group and said electron-accepting leaving group from said compound.

12. A process of claim 11 wherein the dielectric constant at room temperature of said inert, aprotic organic solvent is at least 15.

13. A process of claim 12 wherein said inert, aprotic organic solvent is acetonitrile.

14. A compound of the formula

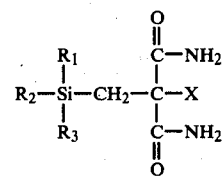

wherein $R_1$, $R_2$, and $R_3$ each can independently be lower alkyl of from 1 to 10 carbon atoms, aryl, alkaryl, aralkyl, or halogen, and X is an electron-accepting leaving group.

15. A compound as defined in claim 14 wherein X is selected from the group consisting of chloride, bromide, and iodide; hydroxy; alkoxy; thiol; thioethers; sulfonyl; quaternary nitrogen groups; phosphonium groups; and

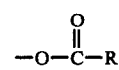

wherein R can be alkyl or aryl.

16. A compound as defined in claim 15 wherein X is chloride.

* * * * *